United States Patent [19]

Vidal et al.

[11] 4,115,428
[45] Sep. 19, 1978

[54] CATALYST AND PROCESS FOR PRODUCING POLYHYDRIC ALCOHOLS AND DERIVATIVES

[75] Inventors: José Luis Vidal, Charleston, W. Va.; Zoltan Csaba Mester, North Tonawanda, N.Y.; Wellington Epler Walker, Sissonville, W. Va.

[73] Assignee: Union Carbide Corporation, New York, N.Y.

[21] Appl. No.: 838,016

[22] Filed: Sep. 29, 1977

[51] Int. Cl.² .................. C07C 27/06; C07C 29/16
[52] U.S. Cl. ........................ 260/449 L; 260/449 R; 260/449.5; 252/443; 423/417
[58] Field of Search ............ 260/449 R, 449 L, 449.5

[56] References Cited

U.S. PATENT DOCUMENTS

| | | | |
|---|---|---|---|
| 3,957,857 | 5/1976 | Pruett et al. | 260/449 R |
| 3,968,136 | 7/1976 | Walker et al. | 260/449 R |

*Primary Examiner*—Howard T. Mars
*Attorney, Agent, or Firm*—Donald M. Papuga

[57] ABSTRACT

A novel catalyst and process for the manufacture of polyhydric alcohols from synthesis gas. This novel catalyst is a rhodium carbonyl carbido cluster compound. In particular the cluster compound is of the following empirical formula:

$$Cs_2[Rh_6(CO)_{15}C]$$

14 Claims, No Drawings

CATALYST AND PROCESS FOR PRODUCING POLYHYDRIC ALCOHOLS AND DERIVATIVES

This invention relates to the production of polyhydric alcohols, in particular alkane polyols, as well as a variety of other chemicals, in particular methanol. The invention is also concerned with a novel catalyst for producing such products from synthesis gas, i.e., a mixture of carbon monoxide and hydrogen.

Polyhydric alcohols are presently being produced synthetically by the oxidation of petroleum derived materials. Owing to the limited availability of petroleum sources, the cost of these petroleum derived materials has been steadily increasing. Many have raised the dire prediction of a significant oil shortage in the future. The consequence of this has been the recognition of the need for a new low cost source of chemicals which can be converted into such polyhydric alcohols.

This invention is directed to the process of making alkane diols, triols, tetraols, etc., containing 2, 3, 4 or more carbon atoms. A key product of the process of this invention is ethylene glycol. By-products of this invention are the lesser valuable, but nonetheless valuable, monohydric alkanols such as methanol, ethanol and propanol. The products of the process of this invention contain carbon, hydrogen and oxygen.

These are described in U.S. Pat. No. 3,833,634, issued Sept. 3, 1974, and U.S. Pat. No. 3,957,857, issued May 18, 1976, processes for reacting hydrogen and oxides of carbon in the presence of rhodium carbonyl complex catalysts. U.S. Pat. No. 3,957,857 is concerned with a rhodium carbonyl complex which is a rhodium carbonyl cluster exhibiting a particular infrared spectrum. The conditions, broadly speaking, employed in those processes involve reacting a mixture of an oxide of carbon and hydrogen with a catalytic amount of rhodium in complex combination with carbon monoxide, at a temperature of between about 100° C. to about 375° C. and a pressure of between about 500 p.s.i.a. to about 50,000 p.s.i.a. As described in these patents, the process is carried out in a homogeneous liquid phase mixture in the presence of one or more ligands selected from among groups referred to in the patent, as organic oxygen ligands, organic nitrogen ligands and organic aza-oxa ligands. In addition to the aforementioned U.S. Patents, the following U.S. Patents and U.S. Patent applications amplify the development of the processes for making alkane polyols from mixtures of hydrogen and oxides of carbon:

| | |
|---|---|
| U.S.P. 3,878,292 | Patented April 15, 1975 |
| U.S.P. 3,878,290 | Patented April 15, 1975 |
| U.S.P. 3,878,214 | Patented April 15, 1975 |
| U.S.P. 3,886,364 | Patented May 27, 1975 |
| U.S.P. 3,940,432 | Patented February 24, 1976 |
| U.S.P. 3,929,969 | Patented December 30, 1975 |
| U.S.P. 3,952,039 | Patented April 20, 1976 |
| U.S.P. 3,948,965 | Patented April 6, 1976 |
| U.S.P. 3,944,588 | Patented March 16, 1976 |
| U.S. Ser. No. 455,380 | Filed March 27, 1974 |
| U.S. Ser. No. 455,379 | Filed March 27, 1974 |
| U.S. Ser. No. 526,942 | Filed November 25, 1974 |
| U.S. Ser. No. 488,139 | Filed July 12, 1974 |
| U.S. Ser. No. 488,140 | Filed July 12, 1974 |
| U.S. Ser. No. 506,862 | Filed September 17, 1974 |
| U.S. Ser. No. 506,864 | Filed September 17, 1974 |
| U.S. Ser. No. 506,865 | Filed September 17, 1974 |
| U.S. Ser. No. 511,740 | Filed October 3, 1974 |
| U.S. Ser. No. 615,093 | Filed September 19, 1975 |
| U.S. Ser. No. 537,885 | Filed January 2, 1975 |
| U.S. Ser. No. 618,023 | Filed September 30, 1975 |
| U.S. Ser. No. 618,061 | Filed September 30, 1975 |
| U.S. Ser. No. 618,021 | Filed September 30, 1975 |
| U.S. Ser. No. 727,646 | Filed September 29, 1976 |
| U.S. Ser. No. 782,986 | Filed March 30, 1977 |

This invention constitutes an addition to or an improvement of the inventions of the foregoing patents and patent applications.

U.S. Pat. No. 3,957,857, issued on May 18, 1976, describes a process for the reaction of synthesis gas in the presence of a rhodium carbonyl cluster which exhibits under certain cicumstances, a specific infrared spectral pattern. The particular cluster chemistry which is involved in that U.S. Patent is valid to date, and remains a significant contribution in the manufacture of the alkane polyols from synthesis gas.

There is described in this application the use as a catalyst in this reaction of a rhodium cluster compound which does not possess the three band infrared spectral pattern which is characterized in U.S. Pat. No. 3,957,857. The cluster compounds which form part of this invention are rhodium carbonyl clusters which possess a carbido molecule directly attached to the rhodium atoms contained in the cluster structure. In addition, there is a novel rhodium carbonyl carbido compound covered by this invention which is a combination of the cluster anion associated with a specific alkali metal cation, to wit, cesium. The structure of the cluster is the specific stoichiometric relationship of cesium to a divalent ionic rhodium carbonyl carbido cluster. The empirical formula for this structure is as follows:

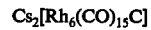

$Cs_2[Rh_6(CO)_{15}C]$

This invention involves the reaction to make polyhydric alcohols in a homogeneous liquid phase system comprising carbon monoxide and hydrogen in combination with a cation and a rhodium carbonyl carbido anion wherein the molar ratio of cesium cation to the anion is two to one. The rhodium carbonyl carbido anion has the structure:

$[Rh_6(CO)_{15}C]^=$

Under pressure conditions in the homogeneous liquid phase, in the presence of $H_2$ and CO, the cluster exhibits an infrared spectral pattern which is characterized by three significant infrared bands at about 1810 cm$^{-1}$, about 1839–40 cm$^{-1}$, and about 1985 cm$^{-1}$, each plus or minus 10 cm$^{-1}$.

Other cations may be used in place of cesium. These cations include other alkali metal cations, organic cations such as $[(C_6H_5)_3P]_2N^+$, $R_4N^+$, $R_{4-n}R_nN^+$, wherein R is alkyl or aryl and $n$ is a positive integer from 0 to 4, and other positively charged species that would form a salt with $[Rh_6(CO)_{15}C]^{2-}$.

The process of this invention which involves the reaction between carbon monoxide and hydrogen in the homogeneous liquid phase mixture, is carried out at a temperature of between about 240° C. to about 280° C., and preferably between about 250° C. and about 270° C., sufficient to produce the alkane polyol. The process is also conducted under superatmospheric pressure. Desirably, the pressure ranges from about 4,000 pounds per square inch absolute (psia) to about 16,000 psia and preferably in the range of about 6,000 psia to about 14,000 psia.

In practicing in the process of this invention, the reaction (or residence) time utilizing the catalyst system which provides the infrared spectral patterns, as afore-described, can range from about fractions of a second to as long as 3 to 4 hours or more, depending upon the conditions selected; milder conditions providing longer residence times whereas more aggressive conditions in terms of pressure and temperature reducing the residence time.

The reaction is effected with a normally liquid organic solvent such as are described in U.S. Pat. Nos. 3,833,634 and 3,957,857. The description of solvents as contained in those patents are incorporated herein by reference. The preferred solvents for practising the invention are a number of solvents which have heretofore been described in the production of alkane polyols from synthesis gas. Particularly desirable solvents are tetraglyme, sulfolane, gamma-butyrolactone and the crown ethers. Other very desirable solvents include mixtures of tetraglyme and sulfolane, mixtures of sulfolane and butyrolactone, mixtures of crown ethers and sulfolane, mixtures of crown ethers and tetraglyme, mixtures of crown ethers and butyrolactone.

The rhodium carbonyl carbido cesium salt can be obtained starting with materials characterized by V. G. Albano et al., *Journal of the Chemical Society*, Dalton Transactions, pages 651–655 (1953), and, in particular, by the experimental procedure which is described at page 651 thereof, wherein the authors characterize the production of the bis-trimethylbenzylammonium decapentacarbonyl hexarhodium carbide. The bis-trimethylbenzylammonium salt of pentadecacarbonyl hexarhodium carbide is converted to either a sodium or potassium salt by a direct transfer or substitution reaction in a solvent, such as methanol, under a carbon monoxide atmosphere. When the solution becomes deep green due to the formation of the hexadecacarbonyl heptarhodium trianion, a chlorinated solvent, such as chloroform or carbon tetrachloride, is then added to effect a yellow-green solution. After adding an excess of solid carbon dioxide, the solution is dried and the residue is dissolved in water. The filtered solution is thereafter saturated with solid potassium chloride and the resultant yellow crystalline precipitate is washed with a saturated solution of potassium bromide, and vacuum dried. The pure potassium bromide salt can be obtained by extraction with tetrahydrofuran, in about 70 percent yield. The potassium salt is dissolved in another alcohol solvent, such as ethanol, and treated with a solution of an ammonium chloride, such as benzyltrimethylammonium chloride, and the resultant yellow precipitate is recrystallized from acetone to isopropanol. In a modification of this method, cesium hydroxide and cesium chloride are used instead of sodium hydroxide and potassium bromide. Three days instead of 2 days are allowed for reaction. The pure cesium salt is prepared in this way with 70-80 percent yield.

The quantity of cluster compound employed is not narrowly critical and can vary over a wide range. In general, the process of preparing alkane diols and derivatives thereof is desirably conducted in the presence of a catalytically effective quantity of the cluster compound which gives a suitable and reasonable reaction rate. Reaction proceeds when employing as little as about $1 \times 10^{-6}$ weight percent, and even lesser amounts, of rhodium (calculated as the metal in the cluster compound) based on the total weight of reaction mixture. The upper concentration limit can be quite high, e.g., about 1 weight percent rhodium and higher, and the realistic upper limit in practicing the invention appears to be dictated and controlled more by economics in view of the exceedingly high cost of rhodium metal and rhodium compounds. No particular advantages at relatively high concentrations of rhodium are manifest. Depending on various factors such as the partial pressures of oxides of carbon and hydrogen, the total operative pressure of the system, the operative temperature, the choice of the normally-liquid organic diluent, and other considerations, a carbido cluster concentration of from about $1 \times 10^{-5}$ to about 10 weight percent rhodium (contained in the complex catalyst) based on the total weight of reaction mixture, is generally desirable in the practice of the invention.

A number of nitrogen containing bases may be used in the catalytic process of the present invention. For the purposes of this invention these nitrogen containing bases can be considered to promote the activity of the instant rhodium catalyst.

Nitrogen Lewis bases used as promoters generally contain hydrogen and nitrogen atoms. They may also contain carbon and/or oxygen atoms. They may be organic or inorganic compounds. With respect to the organic compounds, the carbon atoms can be part of an acyclic and/or cyclic radical such as aliphatic, cycloaliphatic, aromatic (including fused and bridged) carbon radicals, and the like. Preferably, the organic Lewis bases contain from 2 to 60, most preferably 2 to 40 carbon atoms. The nitrogen atoms can be in the form of imino (—N=), amino (—N—), nitrilo (N≡), etc. Desirably, the Lewis base nitrogen atoms are in the form of imino nitrogen and/or amino nitrogen. The oxygen atoms can be in the form of groups such as hydroxyl (aliphatic or phenolic),

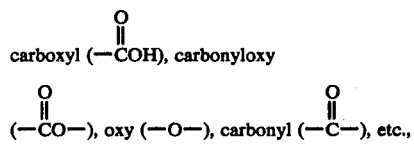

all of said groups containing Lewis base oxygen atoms. In this respect, it is the "hydroxyl" oxygen in the

and the "oxy" oxygen in the

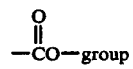

that are acting as Lewis base atoms. The organic Lewis bases may also contain other atoms and/or groups as substituents of the aforementioned radicals, such as alkyl, cycloalkyl, aryl, chloro, trialkylsilyl substituents.

Illustrative of organic aza-oxa Lewis bases are, for example, the alkanolamines, such as, ethanolamine, diethanolamine, isopropanolamine, di-n-propanolamine, and the like; N,N-dimethylglycine, N,N-diethylglycine; iminodiacetic acid, N-methyliminodiacetic acid; N-methyldiethanolamine; 2-hydroxypyridine, 2,4-dihydroxypyridine, 2-methoxypyridine, 2,6-dimethoxypyridine, 2-ethoxypyridine; lower alkyl substituted hydroxypyridines, such as 4-methyl-2-hydroxypyridine, 4- methyl-2,6-dihydroxypyridine, and the like; morpholine, substituted morpholines, such as 4-methylmorpholine, 4-phenylmorpholine; picolinic acid, methyl-substituted picolinic acid; nitrilotriacetic acid, 2,5-dicarboxypiperazine, N-(2-hydroxyethyl) iminodiacetic acid; ethylenediamine-tetraacetic acid; 2,6-dicarboxypyridine; 8-hydroxyquinoline, 2-carboxyquinoline, cyclohexane-1,2-diamine-N,N,N',N'-tetraacetic acid, the tetramethyl ester of ethylenediamine-tetraacetic acid, and the like.

Other Lewis base nitrogen containing compounds include organic and inorganic amines.

Illustrative of such inorganic amines are, e.g., ammonia, hydroxylamine, and hydrazine. Primary, secondary, or tertiary organic amines are promoters. This includes the mono- and polyamines (such as di-, tri-, tetraamines, etc.) and those compounds in which the Lewis base nitrogen forms part of a ring structure as in pyridine, quinoline, pyrimidine, morpholine, hexamethylene tetraamine, and the like. In addition any compound capable of yielding an amino nitrogen under the reaction conditions of the present invention are promoters, as in the case of an amide, such as formamide, cyanamide, and urea, or an oxime. Further illustrative of these Lewis base nitrogen compounds are aliphatic amines such as methylamine, ethylamine, n-propylamine, isopropylamine, octylamine, dodecylamine, dimethylamine, diethylamine, diisoamylamine, methylethylamine, diisobutylamine, trimethylamine, methyldiethylamine, triisobutylamine, tridecylamine, and the like; alphatic and aromatic di- and polyamines such as 1,2-ethanediamine, 1,3-propanediamine, N,N,N',N'-tetramethylenediamine, N,N,N',N'-tetraethylethylenediamine, N,N,N',N'-tetra-n-propylethylenediamine, N,N,N',N'-tetrabutylethylenediamine, o-phenylenediamine, m-phenylenediamine, p-phenylenediamine, p-tolylenediamine, o-tolidene, N,N,N',N'-tetramethyl-p-phenylenediamine, N,N,N',N'-tetraethyl-4,4'-biphenyldiamine, and the like; aromatic amines such as aniline, 1-naphthyl, amine, 2-naphthylamine, p-toluidine, o-3-xylidine, p-2-xylidine, benzylamine, diphenylamine, dimethylaniline, diethylaniline, N-phenyl-1-naphthylamine, bis-(1,8)-dimethylamino-naphthalene, and the like; alicyclic amines such as cyclohexylamine, dicyclohexylamine, and the like; heterocyclic amines such as piperidine; substituted piperidines such as 2-methylpiperidine, 3-methylpiperidine, 4-ethylpiperidine, and 3-phenylpiperidine; pyridine; substituted pyridines such as 2-methylpyridine, 2-phenylpyridine, 2-methyl-4-ethylpyridine, 2,4,6,-trimethylpyridine, 2-dodecylpyridine, 2-chloropyridine, and 2-(dimethylamino)pyridine; quinoline; substituted quinolines, such as 2-(dimethylamino)-6-methoxyquinoline; 4,5-phenanthroline; 1,8-phenanthroline; 1,5-phenanthroline; piperazine; substituted piperazines such as N-methylpiperazine, N-ethylpiperazine, 2-methyl-N-methylpiperazine, 2,2'-dipyridyl, methyl-substituted 2,2;-dipyridyl; ethyl-substituted 2,2'-dipyridyl; 4-triethylsilyl-2,2'-dipyridyl; 1,4-diazabicyclo[2.2.2]octane, methyl substituted 1,4-diazabicyclo[2.2.2]octane, purine and the like.

Also included herein are the use of dimorpholene compounds as described in U.S. patent application Ser. No. 727,645, filed Sept. 29, 1976, which description is incorporated herein by reference.

The promoter provided to the reaction mixture is present in an amount which is equal to or greater than that amount, determined from the promoter's basicity, which achieves the optimum rate of formation of said alkane polyol at said correlated catalyst concentration, temperature and pressure of such reaction mixture as described in commonly assigned copending applications Ser. No. 790,653, filed Apr. 25, 1977 and Ser. No. 618,023, filed Sept. 30, 1975 which are incorporated herein by reference.

The concentration of the promoter will typically be within about 0.001 to about 10 molar. Obviously this range is definitive of the potential scatter of concentrations predicated on the varieties of promoter basicity available.

Under reaction conditions the promoter is preferably used in amounts from about 0.02 to about 40 equivalents of promoter, most preferably from about 0.1 to about 20 equivalent of promoter, for every atom of rhodium in the reaction mixture. The number of equivalents of promoter is equal to the number of atoms of promoter times the number of nitrogen atoms in each molecule.

In practicing the novel method of the present invention, the synthesis of the desired alkane diols and derivatives thereof by the reaction of hydrogen with an oxide of carbon is suitably conducted under operative conditions, as heretofore described, which give reasonable reaction rates and/or conversions.

The relative amounts of oxide of carbon and hydrogen which are initially present in the reaction mixture can be varied over a wide range. In general, the mole ratio of $CO:H_2$ is in the range of from about 20:1 to about 1:20, suitably from about 10:1 to about 1:10, and preferably from about 5:1 to about 1:5.

It is to be understood, however, that molar ratios outside the aforestated broad range may be employed. Substances or reaction mixtures which give rise to the formation of carbon monoxide and hydrogen under the reaction conditions may be employed instead of mixtures comprising carbon monoxide and hydrogen which are used in preferred embodiments in the practice of the invention. For instance, polyhydric alcohols are obtained by using mixtures containing carbon dioxide and hydrogen. Mixtures of carbon dioxide, carbon monoxide and hydrogen can also be employed. If desired, the reaction mixture can comprise steam and carbon monoxide.

The novel process can be executed in a batch, semicontinuous, or continuous fashion. The reaction can be conducted in a single reaction zone or a plurality of reaction zones, in series or in parallel, or it may be conducted intermittently or continuously in an elongated tubular zone or series of such zones. This material of construction should be such that it is inert during the reaction and the fabrication of the equipment should be able to withstand the reaction temperature and pressure. The reaction zone can be fitted with internal and/or external heat exchanger(s) to thus control undue temperature fluctuations, or to prevent any possible "runaway" reaction temperatures due to the exothermic nature of the reaction. In preferred embodiments of the invention, agitation means to vary the degree of mixing of the reaction mixture can be suitably employed. Mixing induced by vibration, shaker, stirrer, rotatory, oscillation, ultrasonic, etc., are all illustrative of the types of agitation means which are contemplated. Such means are available and well-known to the art. The catalyst may be initially introduced into the reaction zone batchwise, or it may be continuously or intermittently introduced into such zone during the course of the synthesis reaction. Means to introduce and/or adjust the reactants, either intermittently or continuously, into the reaction zone during the course of the reaction can be conveniently utilized in the novel process especially to maintain the desired molar ratios of and the partial pressures exerted by the reactants.

As intimated previously, the operative conditions can be adjusted to optimize the conversion of the desired product and/or the economics of the novel process. In a continuous process, for instance, when it is preferred to operate at relatively low conversions, it is generally desirable to recirculate unreacted synthesis gas with-/without make-up carbon monoxide and hydrogen to the reaction. Recovery of the desired product can be achieved by methods well-known in the art such as by distillation, fractionation, extraction, and the like. A fraction comprising rhodium catalyst, generally contained in byproducts and/or normally liquid organic diluent, can be recycled to the reaction zone, if desired. All or a portion of such fraction can be removed for recovery of the rhodium values or regeneration to the active catalyst and intermittently added to the recycle stream or directly to the reaction zone.

The active form of the rhodium carbonyl cluster may be prepared by various techniques as heretofore described. They can be performed and then introduced into the reaction zone or they can be formed in situ.

The equipment arrangement and procedure which provides the capability for determining the existence of anionic rhodium carbonyl complexes or clusters having defined infrared spectrum characteristics, during the course of the manufacture of polyhydric alcohols from carbon monoxide and hydrogen, pursuant to this invention is disclosed and schematically depicted in U.S. Pat. No. 3,957,857, the disclosure of which is incorporated herein by reference.

A particularly desirable infrared cell construction is described in U.S. Pat. No. 3,886,364, issued May 27, 1975, and its disclosure of a preferred cell construction is incorporated herein by reference.

The "oxide of carbon" as covered by the claims and as used herein is intended to mean carbon monoxide and mixtures of carbon dioxide and carbon monoxide, either introduced as such or formed in the reaction. Preferably, the oxide of carbon is carbon monoxide.

The following examples are merely illustrative and are not presented as a definition of the limits of the invention:

EXAMPLE 1

Preparative Method and Analytical Results For $Cs_2[Rh_6(CO)_{15}C]$

Preparation of $[Rh_6(CO)_{15}C]^{2-}$ salts of $K^+$ and $[(PhCH_2)ME_3]^+$. Dodeca-carbonyltetrarhodium (1 g) was added to a solution of sodium hydroxide (2.14 g) in methanol (30 ml) under carbon monoxide. After 2 hours the solution became deep green due to formation of the anion, $[Rh_7(CO)_{16}]^{3-}$. Addition of $CHCl_3$ (3 ml) gave a slow transformation (2 days) into a yellow-green solution. After addition of excess of solid carbon dioxide the solution was evaporated to dryness and the residue was dissolved in water (25 ml). The filtered solution was saturated with solid KCl (ca. 10 g), and the yellow crystalline precipitate washed with a saturated solution of KBr, and vacuum dried. The pure carbido potassium salt could be obtained by extraction with tetrahydrofuran in ca. 70% yields. The potassium carbido salt (0.5 g) dissolved in ethanol (20 ml) was treated with a solution of benzyltrimethyl-ammonium chloride (1 g) in ethanol (15 ml). The yellow precipitate, potassium carbido salt, was recrystallised from acetone-isopropanol; the yield is quantitative (Found: C, 32.25; H, 2.3; N, 1.90%. Calc. for $C_{36}H_{32}N_2O_{15}Rh_6$: C, 32.0; H, 2.4; N, 2.05%).

A modification of the published method is done by using CsCl instead of KBr, and by allowing 3 instead of 2 days of reaction. The method is a scale up using the following ingredients and amounts: 4.0 g of $Rh_4(CO)_{12}$, 8.56 g of NaOH in 120 ml. of methanol and a solution of 40g of CsCl in 100 ml of water. The pure cesium salt of $[Rh_6(CO)_{15}C]^{2-}$ is prepared in this way with 70–80% yield.

| Elemental Analysis of $Cs_2[Rh_6(CO)_{15}C]$: | | |
|---|---|---|
| | % CALC. | % Found |
| C | 14.62 | 14.77 |
| Cs | 20.20 | 19.96 |
| Rh | 46.72 | 47.40 |

EXAMPLE 2

A 150 ml. capacity stainless steel reactor capable of withstanding pressures up to 7,000 atmospheres was charged with a premix of 75 cubic centimeters (cc) of solvent, 3.0 millimoles (mmol), 0.77 grams, of rhodium carbonyl carbide cluster compound of the following formula:

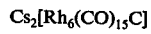

$Cs_2[Rh_6(CO)_{15}C]$

The reactor was sealed and charged with a gaseous mixture, containing equal molar amounts of carbon monoxide and hydrogen, to a pressure of 8,000 pounds per square inch (psig). Heat was applied to the reactor and its contents; when the temperature of the mixture inside the reactor reached 260° C., as measured by a suitably placed thermocouple, an additional adjustment of carbon monoxide and hydrogen ($H_2:CO=1:1$ mole ratio) was made to bring the pressure back to 8000 psig. The temperature (in ° C.) was maintained at the desired value for 4 hours. During this period of time additional carbon monoxide and hydrogen was added whenever the pressure inside the reactor dropped below about 7500 psig. With these added repressurizations the pressure inside the reactor was maintained at 8000 psig ± 400 psig over the entire 4 hour period.

After the 4 hour period, the vessel and its contents were cooled to room temperature, the excess gas vented and the reaction product mixture was removed. Analysis of the reaction product mixture was made by gas chromatographic analysis using a Hewlett Packard FM ™ model 810 Research Chromatograph.

Rhodium recovery was determined by atomic absorption analysis of the contents of the reactor after the venting of the unreacted gases at the end of the reaction. A further analysis was run on a "wash" of the reactor. The wash of the reactor consisted of charging to the reactor 100 cc of the solvent used for that experiment, and bringing the reactor and its contents to a temperature of 160° C. and a pressure of 14,000 to 15,000 psig and maintaining these conditions for a period of 30 minutes. The reactor was then cooled and the unreacted gases vented and an atomic absorption analysis for rhodium was run on the reactor's contents. The rhodium recovery values recited below are the percent rhodium based on the total rhodium charged to the reactor that is soluble or suspended in the reaction mixture plus the wash after the specified reaction time.

The temperature, pressure, solvent, analysis of the product mixture, rhodium charged to the system and rhodium recovery are set forth in the TABLE.

EXAMPLES 3 to 21

The same equipment and procedure used in Example 2 were used in all the Examples except that an amine promoter was added to the reaction mixture and except for the conditions specified.

The promoter, temperature, pressure, solvent, analysis of the product mixture, rhodium charged to the system and rhodium recovery are set forth in the TABLE.

TABLE
CATALYTIC ACTIVITY OF $Cs_2[Rh_6(CO)_{15}C]$

| Examples | Promoter (mmoles) | T (° C) | $P^a$ (psig) | Solvent[b] | Rate(Mole,Liter$^{-1}$ Hour$^{-1}$) $CH_3OH$ | $HO\ CH_2CH_2OH$ | Rh(mmoles) | % Rh Recovered In Solution |
|---|---|---|---|---|---|---|---|---|
| 2 | — | 250 | 8000 | Sulfolane | 4.4 | 1.3 | 3.0 | 90 |
| 3 | $CH_3N(CH_2CH_2)_2O$, (5.0) | 250 | 8000 | " | 3.3 | 4.3 | 3.0 | 100 |
| 4 | $C_5H_5N$,(1.25) | 250 | " | " | 2.7 | 3.2 | 3.0 | 93 |
| 5 | " | 260 | " | " | 5.6 | 7.2 | " | 89 |
| 6 | " | 270 | " | " | 2.4 | 1.6 | " | 71 |
| 7 | "(0.63) | 240 | 15000 | Tetraglyme | 1.3 | 1.3 | 1.5 | 72 |
| 8 | $C_5H_5N$, (0.63) | 240 | " | Tetr/Sulf | 0.23 | 0.57 | 1.5 | 85 |
| 9 | " | 260 | " | " | 1.4 | 2.4 | " | 90 |
| 10 | " | 270 | " | " | 2.3 | 2.9 | " | 87 |
| 11 | " | 280 | " | " | 3.2 | 2.6 | " | 82 |
| 12 | $CH_3N(CH_2CH_2)_2O$, (3.0) | 240 | " | " | 0.3 | 0.7 | " | 90 |
| 13 | " | 260 | " | " | 1.5 | 2.4 | " | 91 |
| 14 | " | 270 | " | " | 2.2 | 3.0 | " | 87 |
| 15 | " | 280 | " | " | 2.8 | 3.2 | " | 82 |
| 16 | $[O(CH_2CH_2)N]_2 (CH_2CH_2)$,(4.0) | 240 | " | " | 0.3 | 0.5 | " | 97 |
| 17 | " | 260 | " | " | 1.4 | 1.0 | " | 90 |
| 18 | " | 270 | " | " | 2.5 | 3.4 | " | 98 |
| 19 | " | 280 | " | " | 4.0 | 3.6 | " | 78 |
| 20 | " | 290 | " | " | 5.6 | 3.3 | " | 59 |
| 21[c] | $CH_3N(CH_2CH_2)_2O$, (5.0) | 260 | 12500 | " | 1.4[c] | 2.4[c] | 3.0 | 89 |

[a]Reaction time for 8000 psig runs is 4 hours; while 15000 psig runs are conducted up to 1 hour or 6000 psig gas uptake whatever happens first.
[b]Tetraglyme-Sulfolane 50%-50% volume mixture.
[c]Reaction time for this run is 0.25 h, and the productivity of methanol and ethylene glycol is given in grams.

What is claimed is:

1. The process of making an alkane polyol (s) which comprises reacting in a homogeneous liquid phase a mixture of hydrogen and oxides of carbon in the presence of a rhodium carbonyl carbido cluster at a pressure between about 4000 to about 16,000 pounds per square inch absolute and at a temperature of between about 240° C. and about 280° C. sufficient to form such alkane polyol.

2. The process of claim 1 wherein the rhodium carbonyl carbido cluster which possesses an infrared spectrum which is characterized by three significant infrared bands between about plus and minus 10 cm$^{-1}$ of about 1810 cm$^{-1}$, about 1839–40 cm$^{-1}$ and about 1985 cm$^{-1}$.

3. The process of claim 2 wherein the rhodium carbonyl carbido cluster is of the following formula:

$$Cs_2[Rh_6(CO)_{15}C]$$

4. The process of claim 1 wherein the rhodium carbonyl cluster compound is dissolved in a solvent.

5. The process of claim 4 wherein the solvent is tetraglyme.

6. The process of claim 4 wherein the solvent is sulfolane.

7. The process of claim 1 wherein the temperature of the reaction is between 250° C. and about 270° C.

8. The process of claim 1 wherein the process is conducted under a pressure of between 6,000 to about 14,000 pounds per square inch absolute.

9. The process of claim 1 wherein the alkane polyol is ethylene glycol.

10. The process of claim 1 wherein the principal products recovered are ethylene glycol and methanol.

11. The process of claim 1 wherein the reaction is effected in the presence of a nitrogen containing base promoter.

12. The process of claim 11 wherein the promoter is pyridine.

13. The process of claim 11 wherein the promoter is N-methylmorpholine.

14. The process of claim 11 wherein the promoter is ethylene dimorpholine.

* * * * *